US012758585B2

(12) United States Patent
Kang et al.

(10) Patent No.: US 12,758,585 B2
(45) Date of Patent: Oct. 13, 2026

(54) VACCINE COMPRISING NATURAL KILLER CELLS LOADED WITH LIGANDS OF NATURAL KILLER T CELLS AND CANCER ANTIGENS

(71) Applicant: CELLID CO., LTD., Seoul (KR)

(72) Inventors: Chang-Yuil Kang, Seoul (KR); Boyeong Song, Seoul (KR); Insu Jeon, Seoul (KR)

(73) Assignee: CELLID CO., LTD., Seoul (KR)

( * ) Notice: Subject to any disclaimer, the term of this patent is extended or adjusted under 35 U.S.C. 154(b) by 0 days.

(21) Appl. No.: 18/873,212

(22) PCT Filed: May 19, 2023

(86) PCT No.: PCT/KR2023/006867

§ 371 (c)(1),
(2) Date: Dec. 9, 2024

(87) PCT Pub. No.: WO2023/243890

PCT Pub. Date: Dec. 21, 2023

(65) Prior Publication Data

US 2025/0170179 A1 May 29, 2025

(30) Foreign Application Priority Data

Jun. 15, 2022 (KR) ........................ 10-2022-0072485
Feb. 28, 2023 (KR) ........................ 10-2023-0027127

(51) Int. Cl.

| | |
|---|---|
| ***A61K 35/17*** | (2025.01) |
| ***A61K 39/00*** | (2006.01) |
| ***A61K 39/12*** | (2006.01) |
| ***A61K 40/15*** | (2025.01) |
| ***A61K 40/42*** | (2025.01) |
| ***A61P 35/00*** | (2006.01) |
| ***C12N 7/00*** | (2006.01) |
| ***C12N 15/86*** | (2006.01) |

(52) U.S. Cl.

CPC .......... *A61K 35/17* (2013.01); *A61K 39/0012* (2013.01); *A61K 39/12* (2013.01); *A61K 40/15* (2025.01); *A61P 35/00* (2018.01); *C12N 7/00* (2013.01); *C12N 15/86* (2013.01); *A61K 2039/5156* (2013.01); *A61K 2039/53* (2013.01); *A61K 2039/572* (2013.01); *C12N 2710/10043* (2013.01); *C12N 2710/20034* (2013.01)

(58) Field of Classification Search

None

See application file for complete search history.

(56) References Cited

U.S. PATENT DOCUMENTS

| | | | |
|---|---|---|---|
| 7,488,491 B2 | 2/2009 | Tsuji et al. | |
| 10,124,023 B2 | 11/2018 | Brentjens et al. | |
| 12,195,759 B2 | 1/2025 | Lee et al. | |
| 2006/0211856 A1 | 9/2006 | Tsuji et al. | |
| 2025/0000969 A1 * | 1/2025 | Choudhry ............ | A61K 35/545 |
| 2025/0170179 A1 | 5/2025 | Kang et al. | |

FOREIGN PATENT DOCUMENTS

| | | | |
|---|---|---|---|
| CN | 113293138 | A | 8/2021 |
| EP | 2029165 | * | 3/2014 |
| JP | 2005-500336 | A | 1/2005 |
| KR | 1020070105662 | A | 10/2007 |
| KR | 100809873 | B1 | 3/2008 |
| KR | 1020090051598 | A | 5/2009 |
| KR | 101055666 | B1 | 8/2011 |
| KR | 1020190129424 | A | 11/2019 |
| KR | 1020210108497 | A | 9/2021 |
| KR | 10-2023-0172384 | A | 12/2023 |
| WO | 2024058609 | A1 | 3/2024 |

OTHER PUBLICATIONS

Jin et al, Hitting the complexity of the TIGIT-CD96-CD112R-CD226 axis for next-generation cancer immunotherapy, BMB Rep. 2021; 54(1): pp. 2-11.*

Zeng et al, The CD112R/CD112 axis: a breakthrough in cancer immunotherapy, Journal of Experimental & Clinical Cancer Research (2021), pp. 1-11.*

Carlsten et al, efficient mrna-Based genetic engineering of human nK cells with high-affinity cD16 and ccr7 augments rituximab-induced aDcc, frontiers in Immunology, 2016, pp. 1-9.*

Bendelac et al. (2007). The biology of NKT cells. Annu. Rev. Immunol., 25(1), 297-336.

(Continued)

*Primary Examiner* — Maria Marvich

(74) *Attorney, Agent, or Firm* — Caesar Rivise, PC

(57) ABSTRACT

The present invention relates to an immunotherapeutic and preventive vaccine including natural killer cells loaded with ligands of natural killer T cells and cancer antigens, and more particularly, to an immunotherapeutic or preventive vaccine including natural killer cells loaded with alpha-galactosylceramide (α-GC), which is a natural killer T cell ligand and a type of glycolipid. The composition of the present invention can be used as an anticancer immuno-therapeutic agent because natural killer cells are easier to obtain than dendritic cells, and immunization with natural killer cells loaded with ligands of natural killer T cells and antigens induces significant levels of cytotoxic T lymphocyte responses as well as therapeutic effects on malignant tumors.

5 Claims, 11 Drawing Sheets

(56) References Cited

OTHER PUBLICATIONS

Chung et al. (2006). CD1d-restricted T cells license B cells to generate long-lasting cytotoxic antitumor immunity in vivo. Cancer research, 66(13), 6843-6850.
Chung et al. (2012). T cells and T cell tumors efficiently generate antigen-specific cytotoxic T cell immunity when modified with an NKT ligand. Oncoimmunology, 1(2), 141-151.
Giaccone et al. (2002). A phase I study of the natural killer T-cell ligand α-galactosylceramide (KRN7000) in patients with solid tumors. Clinical Cancer Research, 8(12), 3702-3709.
Hayakawa et al. (2001). Critical contribution of IFN-γ and NK cells, but not perforin-mediated cytotoxicity, to anti- metastatic effect of α-galactosylceramide. European journal of immunology, 31(6), 1720-1727.
Kaer, L.V. (2005). α-Galactosylceramide therapy for autoimmune diseases: prospects and obstacles. Nature Reviews Immunology, 5(1), 31-42.
Kawano et al. (1997). CD1d-restricted and TCR-mediated activation of Vα14 NKT cells by glycosylceramides. Science, 278(5343), 1626-1629.
Nieda et al. (2004). Therapeutic activation of Vα24+ Vβ11+ NKT cells in human subjects results in highly coordinated secondary activation of acquired and innate immunity. Blood, 103(2), 383-389.
Nakagawa et al. (1998). Treatment of hepatic metastasis of the colon26 adenocarcinoma with an α-galactosylceramide, KRN7000. Cancer research, 58(6), 1202-1207.
Shimasaki et al. (2020). NK cells for cancer immunotherapy. Nature reviews Drug discovery, 19(3), 200-218.
Shimizu et al. (2007). Tumor cells loaded with α-galactosylceramide induce innate NKT and NK cell-dependent resistance to tumor implantation in mice. The Journal of Immunology, 178(5), 2853-2861.
Uzhachenko et al. (2019). CD8+ T lymphocyte and NK cell network: circuitry in the cytotoxic domain of immunity. Frontiers in immunology, 10, 1906, 1-7.
Van Der Vliet et al. (2001). Potent expansion of human natural killer T cells using α-galactosylceramide (KRN7000)-loaded monocyte-derived dendritic cells, cultured in the presence of IL-7 and IL-15. Journal of immunological methods, 247(1-2), 61-72.
Vivier et al. (2011). Innate or adaptive immunity? The example of natural killer cells. science, 331(6013), 44-49.
English abstract for KR 101055666 B1 (2011).
English abstract for KR 1020070105662 A (2007).
English abstract for KR 1020090051598 A (2009).
English abstract for KR 1020190129424 A (2019).
English-language translation of KR 100809873 B1 (2008).
Erokhina et al. (2019). Extracellular form of heat shock protein HSP70: possibilities of using exogenous HSP70 for combined NK cell therapy. Genes and Cells, v. 14, N. S, p. 90.
Fernandez et al. (2012). Ex-vivo α-Galactosylceramide activation of NKT cells in humans and macaques. Journal of Immunological Methods, 382(1-2): 150-159.
Shimizu et al. (2013). Vaccination with antigen-transfected, NKT cell ligand-loaded, human cells elicits robust in situ immune responses by dendritic cells. Cancer Res, vol. 73, N. 1, pp. 62-73.
English Abstract for WO 2024058609 A1 (2024).
Cellid: "Mechanism", web.archive.org/web/20210413184433/http://cellid.co.kr/eng/company/e01/ (Apr. 13, 2021), XP093288439.
Cellid: "Technical Competence" https://web.archive.org/web/20210413185945/http://cellid.co.kr/eng/company/e01/ (Apr. 13, 2021), XP093288441.
Oncohema Key. Regulation of antigen presentation by dendritic cells and its application to cancer immunotherapy. oncohemakey.com/regulation-of-antigen-presentation-by-dendritic-cells-and-its-application-to-cancer-immunotherapy/ (2016).
International Search Report of PCT/KR2023/006867 mailed Aug. 21, 2023.
Son et al. "Cancer vaccines." Immune Network 5, No. 2 (2005): 55-67, abstract, Table I and II and figures only.
Broderick. (2020). Vaccine BVAC-C shows early promise in cervical cancer. OneLive (https://www.onclive.com/view/vaccine-bvacc-shows-early-promise-in-cervical-cancer).
Choi et al. (2020). Phase I study of a B cell-based and monocyte-based immunotherapeutic vaccine, BVAC-C in human papillomavirus type 16- or 18-positive recurrent cervical cancer. Journal of Clinical Medicine, 9(1), 147. doi:10.3390/jcm9010147.
Abstract: Choi et al. Phase IIa study of BVAC-C in HPV type 16 or 18 positive recurrent cervical carcinoma. J. Clin. Oncol., 2021, DOI:10.1200/JCO.2021.39.15_suppl.5512.
Abstract: Lee et al. First-in-human phase I study of BVAC-B cell therapy in HER2-positive advanced gastric cancer. J. Clin. Oncol., 2020, DOI:10.1200/JCO.2020.38.15_suppl.4534.
Slauenwhite et al. "Regulation of NKT Cell Localization in Homeostasis and Infection", Frontiers In Immunology, vol. 6, (2015), XP093381278, Lausanne, CH ISSN: 1664-3224.
Wagner et al. (2021). Soluble and exosome-bound α-galactosylceramide mediate preferential proliferation of educated nk cells with increased anti-tumor capacity. Cancers, 13, 298.
RIKEN. Developing cancer immunotherapy that activates both innate and adaptive immunity-Utilizing antigen uptake and maturation of in vivo dendritic cells to eliminate a variety of cancer cells. RIKEN Press Release, 2012, https://www.riken.jp/press/2012/20121226/index.html.

* cited by examiner

VACCINE COMPRISING NATURAL KILLER CELLS LOADED WITH LIGANDS OF NATURAL KILLER T CELLS AND CANCER ANTIGENS

CROSS-REFERENCE TO RELATED APPLICATIONS

This application is a U.S. National Stage application filed under 35 U.S.C. § 371 of International Application No. PCT/KR2023/006867 filed May 19, 2023, which claims the benefit of Korean Application Nos. KR 10-2022-0072485, filed Jun. 15, 2022 and KR10-2023-0027127 filed on Feb. 28, 2023. The contents of said applications are incorporated herein by reference in their entireties for all purposes.

BACKGROUND OF THE INVENTION

1. Field of the Invention

The present invention relates to a vaccine comprising natural killer cells loaded with ligands of natural killer T cells and cancer antigens.

2. Description of the Related Art

Natural killer cells are well known as important innate immune cells that prevent the development, growth, and metastasis of cancer by eliminating cancer cells and virus-infected cells through degranulation of cytotoxic granules containing perforin and granzyme, death receptor-mediated apoptosis, and IFN-γ production (Vivier et al., *Science,* 331: 44-49, 2011). Although similar to cytotoxic $CD8^+$ T cells in that they cause cytotoxicity to target cells, natural killer cells, unlike cytotoxic T cells, have no antigen specificity, do not require sensitization or immunization, and can kill cancer cells with low MHC class I expression that cytotoxic T cells cannot attack, thus playing a unique role in anticancer immunity (Uzhachenko and Shanker., *Frontiers in Immunology,* 10: 1906, 2019). Due to the unique characteristics of natural killer cells that are different from cytotoxic $CD8^+$ T cells, active research is being conducted on anticancer immunotherapy focusing on enhancing the cytotoxic capabilities of natural killer cells such as CAR-NKs (Chimeric Antigen Receptor-NKs) (Shimasaki et al., *Nature Reviews Drug Discovery,* 19: 200-218, 2020).

Invariant natural killer T cells (iNKTs) are innate immune cells that express invariant T cell receptors and are known to play an important role in various immune diseases such as cancer, infectious diseases, and autoimmune diseases, mainly through cytokine secretion (Bendelac et al., *Annual Review of Immunology,* 25: 297-336, 2007). Alpha-galactosylceramide (α-GC), a representative ligand of natural killer T cells, is a glycolipid extracted from the sponge Agelas-mauritianus. It is presented by the CD1d molecule and binds to the $V\alpha 14\text{-}J\alpha 18^+$ T cell receptor of natural killer T cells, thereby activating invariant natural killer T cells (Kawano et al., *Science,* 278: 1626-1629, 1997). Natural killer T cells activated by α-GC rapidly produce various cytokines such as IL-4 and IFN-γ, which activate natural killer cells and induce acquired immune responses, including maturation of dendritic cells and activation and differentiation of T cells and B cells (Kaer et al., *Nature Reviews Immunology,* 5: 31-42, 2005).

It has been reported that cancer cells loaded with α-GC can also function as antigen-presenting cells capable of inducing natural killer T cell and natural killer cell responses and cancer antigens-specific T cell immune responses (Shimizu et al., *The Journal of Immunology,* 178: 2853-2861, 2007 & Chung et al., *OncoImmunology,* 1:2, 141-151, 2012). It has also been shown that α-GC-loaded B cells or T cells delivered with antigens via peptide or viral vectors can also acquire the characteristics of antigen-presenting cells (Chung et al., *Cancer Research,* 66: 6843-6850, 2006 & Chung et al., *OncoImmunology,* 1:2, 141-151, 2012). This indicates that α-GC loading and delivery of cancer antigens to cells expressing CD1d molecules can be utilized as a cell vaccine for anticancer therapy.

Accordingly, the present inventors have added the function of antigen-presenting cells by changing the immunogenicity of natural killer cells through loading natural killer T cell ligand, α-GC, on natural killer cells having cytotoxic effects and delivering antigens, and confirmed that the natural killer cells can induce anticancer immune responses, thereby completing the present invention.

SUMMARY OF THE INVENTION

It is an object of the present invention to provide an immunotherapeutic or preventive vaccine comprising natural killer cells loaded with ligands of natural killer T cells and cancer antigens.

To achieve the above object, the present invention provides an immunotherapeutic or preventive vaccine comprising natural killer cells loaded with ligands of natural killer T cells and cancer antigens.

Advantageous Effect

The present invention relates to an immunotherapeutic and preventive vaccine comprising natural killer cells loaded with ligands of natural killer T cells and cancer antigens, and more particularly, to an immunotherapeutic or preventive vaccine comprising natural killer cells loaded with alpha-galactosylceramide (hereinafter, α-GC), which is a natural killer T cell ligand and a type of glycolipid. The composition of the present invention can be used as an anticancer immunotherapeutic agent because natural killer cells are easier to obtain than dendritic cells, and immunization with natural killer cells loaded with ligands of natural killer T cells and antigens induces significant levels of cytotoxic T lymphocyte responses as well as therapeutic effects on malignant tumors.

DESCRIPTION OF THE PREFERRED EMBODIMENTS

Figure 1A:
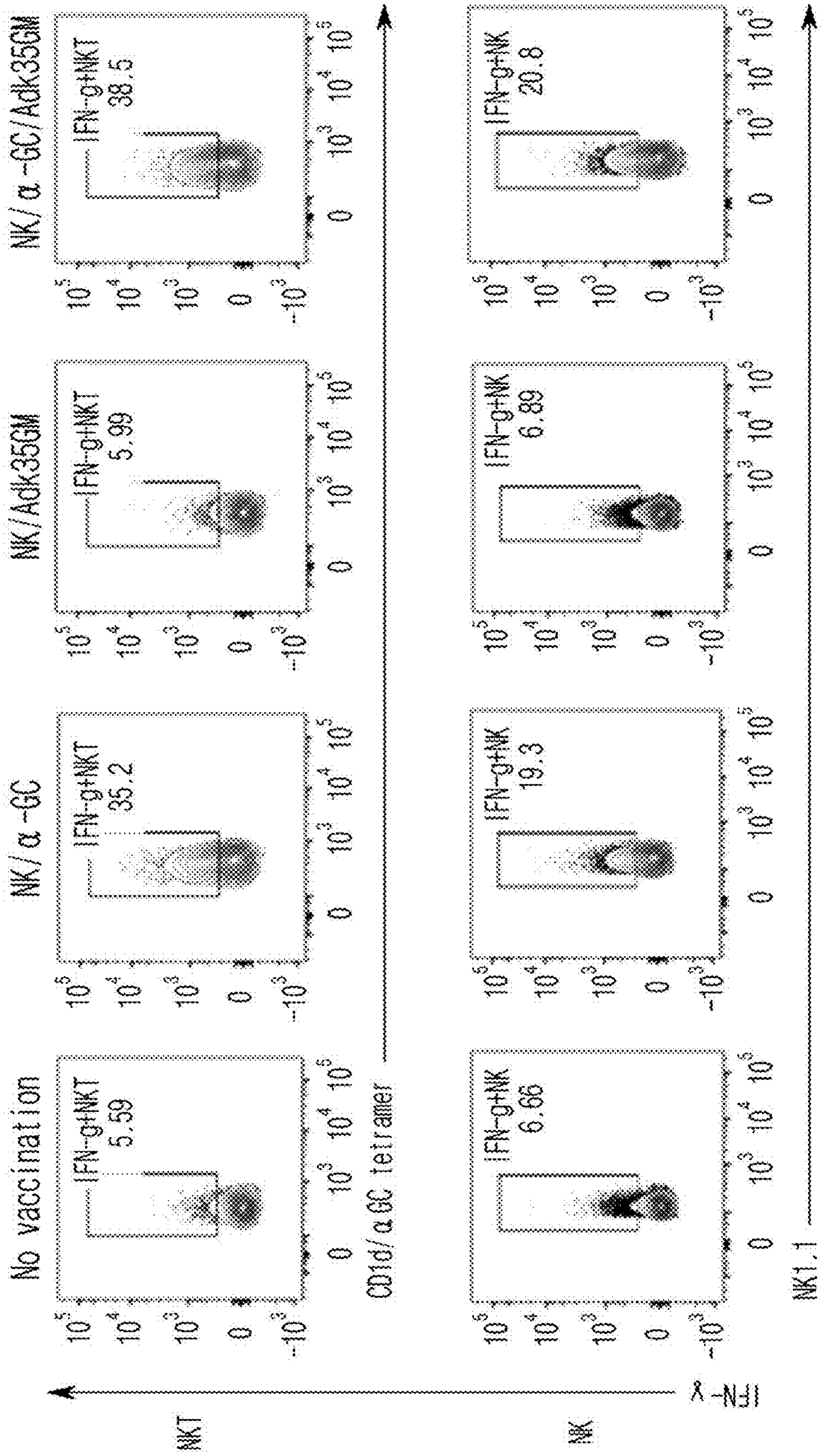
FIG. 1A is a diagram showing the IFN-γ production capacity of natural killer T cells (NKT) and natural killer cells (NK) in the spleen induced by the vaccine comprising natural killer cells loaded with α-GC and/or transected with adenovirus expressing antigens.

Hereinafter, the present invention is described in detail.

It is well known that dendritic cells (DCs) loaded with alpha-galactosylceramide (α-GC) activate invariant natural killer T (NKT) cells (van der Vliet H J, et al., J Immunol Methods., 1; 247 (1-2):61-72, 2001). The present inventors confirmed the effect of inducing cytotoxic T lymphocyte responses in B cells, monocytes, and immature myeloid cells loaded with α-GC (Korean Patent Publication No. 10-2007-0105662 and Korean Patent Publication No. 10-2009-0051598), and confirmed whether similar effects were observed in natural killer cells loaded with α-GC.

Accordingly, the present inventors produced a vaccine by altering the immunogenicity of natural killer cells through α-GC loading and antigen delivery to natural killer cells with cytotoxic effects.

Antigen delivery using viral vectors can deliver cancer antigens to cells with high efficiency, making it suitable for large-scale production of cell therapeutics targeting cancers expressing specific cancer antigens. When a virus capable of expressing the above antigen is used, the entire antigen can be introduced, so it is applicable to all people without being limited to a specific haplotype of the major histocompatibility complex, and has the advantage of being able to induce not only a cellular immune response but also a humoral immune response. On the other hand, viral vectors are limited in their application to personalized cancer therapy.

The method of antigen delivery through peptide loading, when used clinically, is limited to the haplotype of an individual's major histocompatibility complex (MHC), so it cannot be used universally, and has the disadvantage of presenting only a single epitope. However, neoepitopes, the peptide sequences that are created by highly tumor-specific mutations that exist only in cancer cells, not normal cells, and can induce cancer cell-specific immune responses, are known as ideal targets for personalized anticancer immunotherapy for cancer patients. Anticancer immunotherapy using an immune cell vaccine that delivers neoepitopes discovered for personalized treatment for cancer patients is expected to induce the generation of more cancer cell-specific T cells than conventional immunotherapy, thereby minimizing the side effects of anticancer treatment by preventing damage to normal cells, while simultaneously inducing a strong anticancer treatment effect.

Therefore, natural killer cells were isolated from mice, loaded with α-GC, and a natural killer cell vaccine was constructed by delivering antigens in two ways (either by transferring the antigen gene into a viral vector expressing the antigen or by peptide loading) (see Example 1).

First, the present inventors constructed a natural killer cell vaccine loaded with α-GC and delivered with a viral vector expressing the antigen, and confirmed that administration of the vaccine could activate natural killer T cells and natural killer cells. As a result, it was confirmed that natural killer T cells and natural killer cells were activated in mice that received α-GC-loaded natural killer cells and natural killer cells loaded with α-GC and adenovirus-delivered cancer antigens GP100 and MAGE-A3 (see FIGS. 1A to 1C). In addition, an in vivo CTL assay was performed to determine whether the vaccine could induce a cytotoxic immune response by activating antigen-specific cytotoxic T lymphocytes. As a result, it was confirmed that effective cytotoxic responses were induced by the natural killer cell vaccine loaded with α-GC and delivered with cancer antigens (GP100 and MAGE-A3 or HPV16/18 E6E7) via adenovirus (see FIGS. 2A to 2E). In addition, the anticancer effect of the vaccine was confirmed using HPV16/18 E6E7. As a result, it was confirmed that the vaccine exhibited significant anticancer effects by suppressing tumor size and increasing mouse survival rate (see FIGS. 3A to 3C).

Next, the present inventors constructed a natural killer cell vaccine loaded with α-GC and antigenic peptides and determined whether administration of the vaccine induced cytotoxic T cell responses. As a result, it was confirmed that an effective cytotoxic response was induced by the natural killer cell vaccine loaded with α-GC and $OVA_{257-264}$ peptides (see FIGS. 4A to 4C). In addition, the anticancer effect of the vaccine was investigated, and it was confirmed that it exhibited a significant anticancer effect that suppressed the tumor size and increased the mouse survival rate (see FIGS. 5A to 5C). The natural killer cells of the present invention not only have a cytotoxic function and thus have an anticancer effect by themselves, but also acquire properties as antigen-presenting cells that activate antigen-specific cytotoxic T cell responses by loading ligands of natural killer T cells, especially α-GC, and antigen delivery, thereby improving the therapeutic effect on malignant tumors. Therefore, a vaccine composition containing the above cells can be used as a cancer treatment agent.

The ligands of the above natural killer T cells include alpha-galactosylceramide (α-GC), alpha-glucuronosylceramide, phosphatidylinositol tetramannoside, isoglobotrihexosylceramide, ganglioside GD3, phosphatidylcholine, phosphatidylethanolamine, phosphatidylinositol, sulfitide, beta-galactosylceramide, lipophosphoglycan, glycoinositol phospholipids, beta-anomericgalactosylceramide and alpha-anomericgalactosylceramide, which are analogues of alpha-galactosylceramide, bacterial lipid antigens, and variants of alpha-galactosylceramide.

The above antigen may be any antigen that can be used as a vaccine and induce an immune response, and includes antigens derived from pathogens including pathogenic bacteria, viruses, and parasites, or cancer antigens, and can be the full length or a fragment of the above antigen.

The antigens derived from the pathogenic bacteria include *Bordetella pertussis* antigens (pertussis toxin, filamentous haemagglutinin, and pertactin), tetanus toxoid, diphtheria toxoid, Helicobacterpylori antigens (capsular polysaccharides of serogrups A, B, C, Y, and W-135), pneumococcal antigen (*Streptococcus pnemoniae* type 3 capsular polysaccharide), tuberculosis antigen, cholera antigen (cholera toxin B subunit), staphylococcal antigen (staphylococcal enterotoxin B), *shigella* antigen (*shigella* polysaccharides), *Borrelia* sp. antigen, *Candida albicans* antigen, and *Plasmodium* antigen.

The antigens derived from the viruses include influenza virus antigens (haemagglutinin and neuraminidase), human papilloma virus (HPV) antigen (glycoprotein), vesicular stomatitis virus antigen (vesicular stomatitis virus glycoprotein), cytomegalovirus (CMV) antigen, hepatitis virus antigens (hepatitis A(HAV), B(HBV), C(HCV), D(HDV) and G(HGV) antigens) (core antigen and surface antigen), respiratory synctytial virus (RSV) antigen, herpes simplex virus antigen, human immunodeficiency virus (HIV) antigens (GP-120, GP-160, p18, Tat, Gag, Pol, Env) and combinations thereof.

The cancer antigens include gp100, melanoma antigen gene (MAGE), human papilloma virus (HPV) E6/E7, tyrosinase, tyrosinase-related protein-1 (TRP-1), tyrosinase-related protein-2 (TRP-2), murinoglobulin 1 (MUC-1), carcinoembryonic antigen (CEA), p53, α-fetoprotein, breast cancer protein expressed by Her-2/neu, proteinase 3, WT-1, PAP, PSA, PSMA, G250, BAGE, GAGE, NY-ESO-1, MART-1, MCIR, Ig Idiotype, CDK4, caspase-8, β-catenin, CIA, BCR/ABL, EBV LMP2a, HCV, HHV-8, 5T4, tumor-specific mutation-derived neoantigens and combinations thereof.

In addition, the antigen may be directly loaded into natural killer cells in the form of peptides, lipopolysaccharides, polysaccharides, glycoproteins, or polynucleotides including DNA and RNA, and can be transfected into natural killer cells by recombinant viruses and expressed and loaded. Compared to the cell vaccine loaded with peptides, the cell vaccine introduced with the entire antigen via viruses are applicable to all people, not limited to the haplotype of the major histocompatibility complex, and can induce immune responses specific to multiple epitopes, and in particular, has the advantage of being able to induce humoral and cellular immune responses simultaneously.

The antigen can be expressed by introducing it through a recombinant virus. The virus introduced into natural killer cells for antigen expression as mentioned above includes adenovirus, retrovirus, vaccinia virus, Pox virus, and Sindbis virus, but not always limited thereto. In addition to the method using viruses, the following methods can be applied for antigen gene delivery: 1) a method of transducing DNA by binding it to liposomes to protect the DNA from enzymatic degradation or to allow it to be taken up into endosomes, 2) a method of increasing the efficiency of DNA delivery into cells by combining a molecular conjugate consisting of a protein or a synthetic ligand to the DNA [ex: asialoglycoprotein, transferrin, polymeric IgA], 3) A method for delivering antigen genes by increasing the efficiency of DNA delivery into cells through a novel DNA delivery system using PTD (protein transduction domain) [ex: Mph-1], and 4) In addition to the above methods, peptides can be used or antigenic proteins can be applied to natural killer cells to cause the natural killer cells to present the antigen.

The vaccine of the present invention can additionally include, in addition to the natural killer T cell ligands and natural killer cells, one or more effective ingredients having the same or similar effect with them. The vaccine can also include, in addition to the above-mentioned effective ingredients, one or more pharmaceutically acceptable carriers for the administration. The pharmaceutically acceptable carrier can be selected or be prepared by mixing more than one ingredients selected from a group consisting of saline, Ringer's solution, buffered saline, dextrose solution, maltodextrose solution, glycerol, and ethanol. Other general additives such as anti-oxidative agent, buffer solution, bacteriostatic agent, etc., can be added. In order to prepare injectable solutions such as aqueous solution, suspension and emulsion, diluents, dispersing agents, surfactants, binders and lubricants can be additionally added. The vaccine of the present invention can further be prepared in suitable forms for each disease or according to ingredients by following a method represented in Remington's Pharmaceutical Science (the newest edition), Mack Publishing Company, Easton PA.

The vaccine of the present invention can be administered by parenterally and the parenteral administration includes subcutaneous injection, intravenous injection, intramuscular injection and intrathoracic injection. To prepare the vaccine as a formulation for parenteral administration, the natural killer cells loaded with ligands of natural killer T cells, the natural killer cells loaded with ligands of natural killer T cells and peptides, or the natural killer cells infected with viruses expressing cancer antigens of the present invention is mixed with a stabilizer or a buffering agent to produce a solution or suspension, which is then formulated as ampoules or vials.

The vaccine of the present invention can be formulated in a variety of forms according to administration pathways. For example, the vaccine of the present invention can be prepared in the form of sterilized solution or suspension for injection, or in the form of freeze-dried formula using freeze-drying technique. The freeze-dried vaccine of the present invention is supposed to be maintained typically at about 4° C. and can be restored in a stabilizing solution containing or not containing an adjuvant such as saline or/and HEPES.

To accomplish the present invention, the effective dose of the vaccine for administration is determined by considering administration method, administration frequency, specific disease under treatment, severity of disease, disease history, whether or not a patient is under co-treatment with other drugs, age, height, weight, health condition and other physical conditions of a patient, but not always limited thereto. In general, as the weight of a patient under treatment increases, the dose of this preparation is preferably increased.

The vaccine can be administered by effective dose to induce immune response in a patient. For example, the vaccine can be administered to human once or a few times a day by the dosage of $1\times10^3$~$1\times10^9$ cells/kg, and more preferably $1\times10^4$ cells/kg~$1\times10^8$ cells/kg. To prepare a natural killer cell vaccine loaded with alpha-galactosylceramide, a medium has to be supplemented with alpha-galactosylceramide at the concentration of 1~2 μg/mℓ per $1\times10^6$~$1\times10^7$ natural killer cells/mℓ. To prepare a natural killer cell vaccine loaded with alpha-galactosylceramide and peptides, a medium has to be supplemented with alpha-galactosylceramide at the concentration of 1~2 μg/mℓ per $1\times10^6$~$1\times10^7$ natural killer cells/mi and peptide at the concentration of 1-10 μg/mℓ per $1\times10^6$~$1\times10^7$ natural killer cells/mℓ.

Alpha-galactosylceramide does not appear to induce toxicity in rodents and monkeys (Nakagawa et al., Cancer Res 58:1202-1207, 1998). No adverse effects were reported even in mice injected with 2200 μg/kg of αGalCer (Giaccone et al., Clin Cancer Res 8:3702, 2002). In ongoing clinical trials, some side effects, such as mild headache, have been reported with systemic administration of αGalCer (Mie Nieda et al., Blood 103:383-389, Giaccone et al., Clin Cancer Res 8:3702, 2002), but these could be prevented by administration of paracetamol, and mild systemic side effects do not necessarily occur in these subjects (Giaccone et al., Clin Cancer Res 8:3702, 2002).

Hereinafter, the present invention will be described in detail by the following examples.

However, the following examples are only for illustrating the present invention, and the contents of the present invention are not limited thereto.

Example 1: Construction of Natural Killer Cell Vaccine

<1-1> Construction of Natural Killer Cell Vaccine in which Antigens are Delivered by Viral Vectors Expressing the Antigens To isolate natural killer cells from mice, the mouse spleen and bone marrow were collected and then homogenized. After lysing red blood cells using ACK lysing buffer (Gibco), T cells, B cells, and neutrophils expressing CD3ε, CD19, or Ly6G on the cell surface were removed using microbeads (Miltenyibiotec), and then CD49b+ cells were obtained using anti-CD49b microbeads (Miltenyibiotec), and pure natural killer cells were isolated using a BD FACSAria III instrument. The natural killer cells isolated and purified as described above were placed in a medium containing serum and IL-2 (5 ng/mL) along with α-GC (1 μg/ml), solvent (DMSO) and/or adenovirus (100 MOI) for cancer antigen (GP100 and MAGE-A3 cancer antigens or E6 and E7 cancer antigens of human papillomavirus HPV types 16 and 18) gene delivery. After centrifugation at 20° C., 2000 rpm for 90 minutes in cell culture plates, the cells were cultured in a $CO_2$ incubator for 14~15 hours (37° C., 80~95% relative humidity, and 5% $CO_2$ concentration) to prepare natural killer cells loaded with α-GC, natural killer cells transformed with adenovirus to express cancer antigens, natural killer cells loaded with α-GC and transformed with adenovirus to express cancer antigens. The prepared natural killer cell vaccine was washed three times with Dulbecco's phosphate buffered saline (DPBS, Welgene), dissolved in DPBS, and administered into the tail vein of mice.

<1-2> Construction of Natural Killer Cell Vaccine Loaded with Antigen Peptides

Viral vectors are suitable gene delivery vehicles for the large-scale production of cell therapeutics targeting cancer cells expressing specific cancer antigens, as they deliver cancer antigens common to cancer cells with high efficiency. However, viral vectors have limitations in applying personalized treatment for cancer patients using neoepitopes, so the present inventors have constructed a natural killer cell vaccine using antigen delivery via peptide loading.

Specifically, the natural killer cells isolated from C57BL/6 mice by the method of Example <1-1> were placed in a medium containing serum and IL-2 (5 ng/mL) together with α-GC (1 μg/mL), solvent (DMSO), and/or $Ovalbumin_{257-264}$ ($OVA_{257-264}$) peptide (2 μg/mL), and cultured in a $CO_2$ incubator for 15~16 hours (37° C., 80~95% relative humidity, and 5% $CO_2$ concentration) to prepare a natural killer cell vaccine loaded with α-GC, a natural killer cell vaccine loaded with $OVA_{257-264}$ peptide, or a natural killer cell vaccine loaded with α-GC and $OVA_{257-264}$ peptide. The prepared natural killer cell vaccine was washed three times with DPBS, dissolved in DPBS, and administered into the tail vein of mice.

Experimental Example 1: Confirmation of Effectiveness of Natural Killer Cell Vaccine in which Antigens are Delivered by Viral Vectors Expressing Antigens <1-1> Confirmation of Induction of Activation of Natural Killer T Cells and Natural Killer Cells The present inventors confirmed whether natural killer T cells and natural killer cells in the body could be activated through the natural killer cell vaccine administration.

Specifically, natural killer cells obtained from C57BL/6 mice were used to generate natural killer cells loaded with α-GC (NK/α-GC), natural killer cells transduced with adenovirus Adk35GM for cancer antigen (human GP100 and MAGE-A3) delivery (NK/Adk35GM), and natural killer cells loaded with α-GC and antigen-delivered with adenovirus Adk35GM (NK/α-GC/Adk35GM). Then, $8.5\times10^4$ natural killer cells were administered intravenously. After 17 hours, the level of IFN-γ production in natural killer T cells and natural killer cells in the spleen was measured by flow cytometry.

Figure 1B:
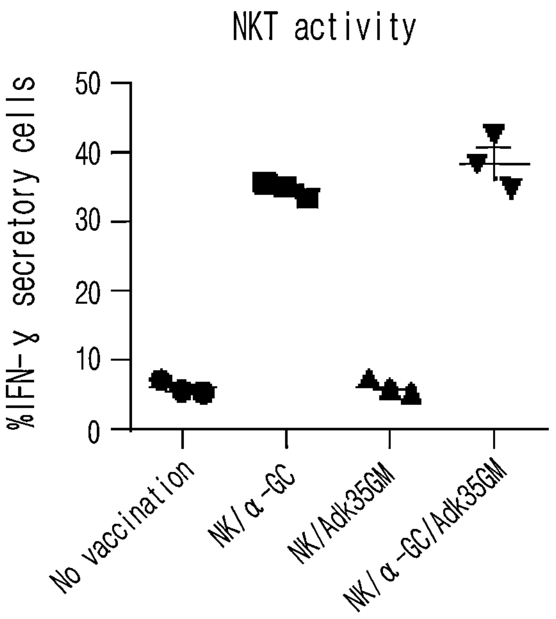
FIG. 1B is a graph showing the IFN-γ production by the natural killer T cells (NKT) of FIG. 1A.
Figure 1C:
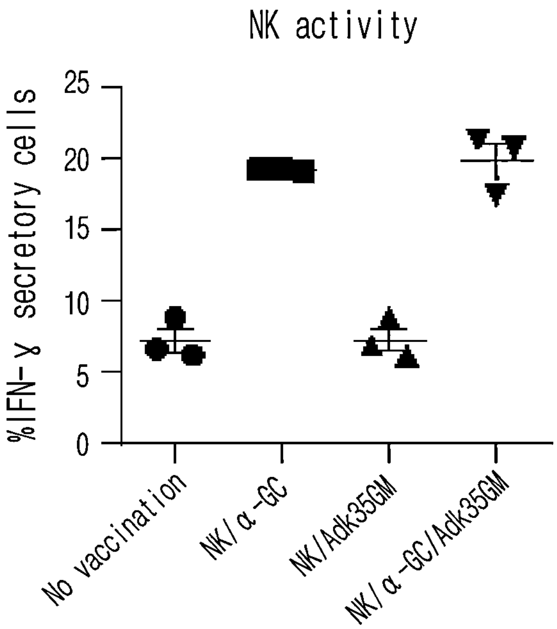
FIG. 1C is a graph showing the IFN-γ production by the natural killer cells (NK) of FIG. 1A.

As a result, as shown in FIGS. 1A to 1C, it was confirmed that the administration of α-GC-loaded natural killer cells (NK/α-GC and NK/α-GC/Adk35GM) to mice stimulated natural killer T cells in the body and consequently activated natural killer cells, unlike the administration of transduced cells (NK/Adk35GM).

It is thought that the activation of these natural killer T cells and natural killer cells may contribute to the anticancer effect along with the induction of cytotoxic T cell responses.

<1-2> Confirmation of Induction of Cytotoxic T Cell Response

<1-2-1> Evaluation of Efficacy of Natural Killer Cell Vaccine Containing GP100 and MAGE-A3

To determine whether the adenovirus-transduced natural killer cell vaccine could induce antigen-specific cytotoxic T cell immune responses, an in vivo CTL assay was performed.

Figure 2A:
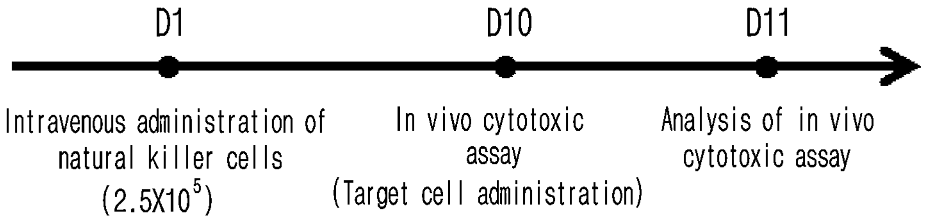
FIG. 2A is a diagram showing the experimental method for confirming the activity of a cytotoxic T cell response by the vaccine comprising natural killer cells loaded with α-GC and/or transected with adenovirus expressing antigens.

Specifically, natural killer cells obtained from C57BL/6 mice were used to construct α-GC-loaded or adenovirus Adk35GM antigen-delivered natural killer cell vaccines, which were immunized into C57BL/6 mice and a cytotoxicity assay was performed 10 days later (FIG. 2A). First, spleen cells from the same mouse were divided into two groups with equal amounts. The target cells loaded with GP100$_{25-33}$ peptide were labeled with 3 μM CFSE (carboxyfluorescein diacetate succinimidyl ester) (CFSE$^{high}$), and the control cells without the peptide were labeled with 0.3 μM CFSE (CFSE$^{low}$), and then injected into the vaccinated mice in equal amounts. One day later, lysis of the target cells was measured by calculating the CFSE$^{high}$: CFSE$^{low}$ ratio in mouse spleen cells by flow cytometry (FIG. 2A). A lower percentage of the CFSE$^{high}$ cells loaded with antigen peptides indicates a higher antigen-specific cytotoxic T cell immune response.

Figure 2B:
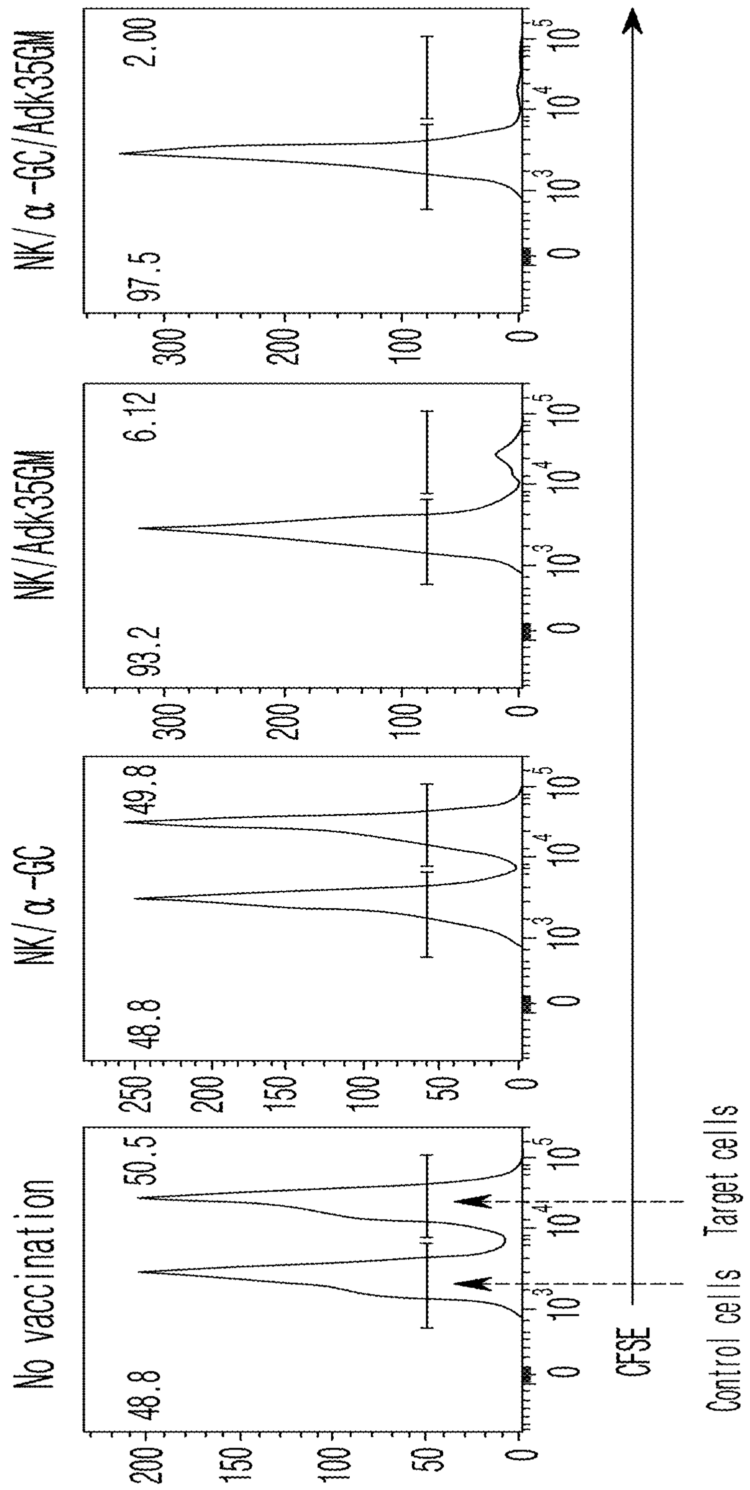
FIG. 2B is a set of histograms showing the results of measuring the in vivo cytotoxic T cell activity after administration of NK/α-GC, NK/Adk35GM, or NK/α-GC/Adk35GM and injection of target cells loaded with $GP100_{25\text{-}33}$ peptide labeled with CFSE.
Figure 2C:
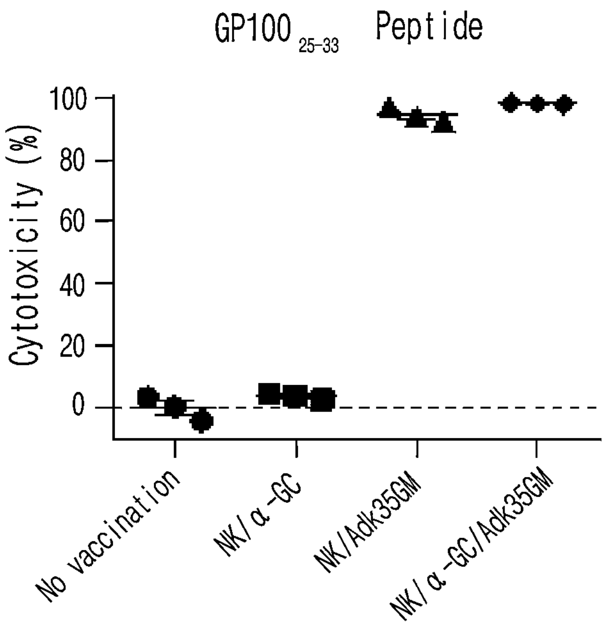
FIG. 2C is a graph showing the cytotoxic T cell activity of FIG. 2B.

As a result, as shown in FIGS. 2B and 2C, when immunized with natural killer cells (NK/Adk35GM, NK/α-GC/Adk35GM) introduced with antigens via adenovirus vector, an effective cytotoxic T cell immune response was observed.

<1-2-2> Evaluation of Efficacy of Natural Killer Cell Vaccine Containing E6 and E7 Antigens of Human Papillomavirus (HPV) Types 16 and 18

To determine whether the natural killer cell-mediated vaccination could be applied to other cancer antigens, the present inventors evaluated the efficacy of a natural killer cell vaccine containing E6 and E7 cancer antigens of human papillomavirus (HPV) types 16 and 18.

Specifically, C57BL/6 mice were immunized with 6.5×10$^5$ natural killer cells loaded with α-GC and engineered to express HPV16/18 E6E7 via adenovirus Ad-E6E7, and then an in vivo cytotoxicity assay was performed 8 days later. The target cells loaded with HPV16 E6$_{49-57}$ and E7$_{49-57}$ peptides were labeled with CFSE$^{high}$, while the control cells were labeled with CFSE$^{low}$ without peptide loading, and the equal amount of cells from both groups were mixed and injected into the immunized mice. One day later, single spleen cells were harvested and the ratio of CFSE$^{high}$ to CFSE$^{low}$ cell populations was measured by flow cytometry.

Figure 2D:
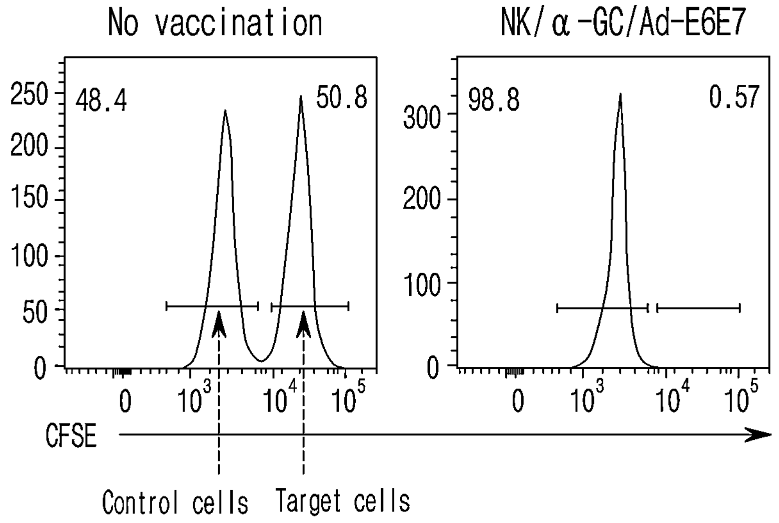
FIG. 2D is a set of histograms showing the results of measuring the in vivo cytotoxic T cell activity after administration of NK/α-GC/Ad-E6E7 and injection of target cells loaded with HPV16 $E6_{49-57}$ 와 HPV16 $E7_{49-57}$ peptides labeled with CFSE.
Figure 2E:
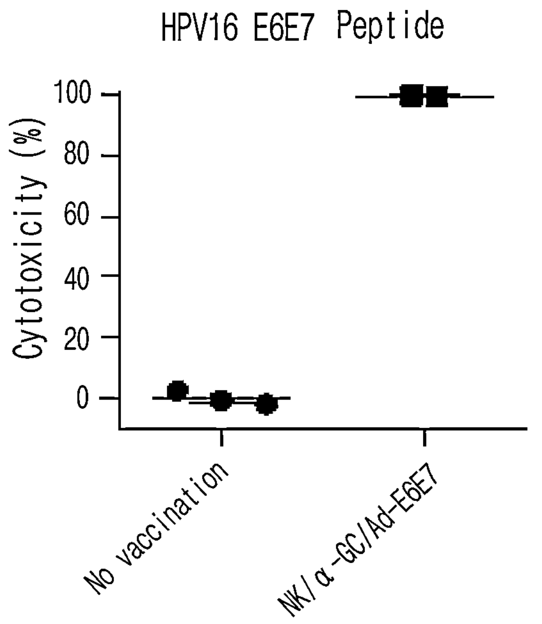
FIG. 2E is a graph showing the cytotoxic T cell activity of FIG. 2D.

As a result, as shown in FIGS. 2D and 2E, cytotoxicity against HPV16 E6E7 was confirmed to be induced in vivo in a group of mice that received natural killer cells loaded with α-GC and engineered to express HPV16/18 E6E7.

Based on the results of Experimental Examples <1-1> and <1-2> above, it can be inferred that both innate immune responses, activation of natural killer T cells and natural killer cells, and acquired immune responses, cytotoxic T cell immune responses, can be induced by administration of a natural killer cell vaccine loaded with α-GC and antigen-delivered by an adenoviral vector, and thus exhibit potent anticancer therapeutic effects.

<1-3> Evaluation of Anticancer Effect of Natural Killer Cell Vaccine

The present inventors investigated whether the natural killer cell vaccine administration induces anticancer immunity.

Figure 3A:
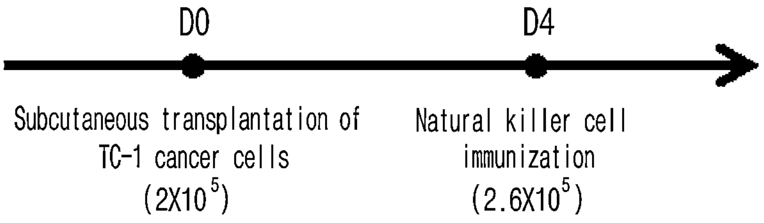
FIG. 3A is a diagram showing the experimental method for confirming the anticancer effect of the vaccine comprising natural killer cells loaded with α-GC and transected with adenovirus expressing antigens.

To this end, C57BL/6 mice were immunized with 2.6×10$^5$ NK/α-GCs or NK/α-GC/Ad-E6E7 4 days after subcutaneous implantation of 2×10$^5$ TC-1 cancer cells into the flanks of C57BL/6 mice (FIG. 3A). Then, tumor size changes and mouse survival rates were measured. The tumor size was calculated using the following equation by measuring the width, length, and height of the tumor using a caliper.

$$(\text{Tumor Size}) = (\text{Width}) \times (\text{Length}) \times (\text{Height}) \times (\pi/6)$$

Figure 3B:
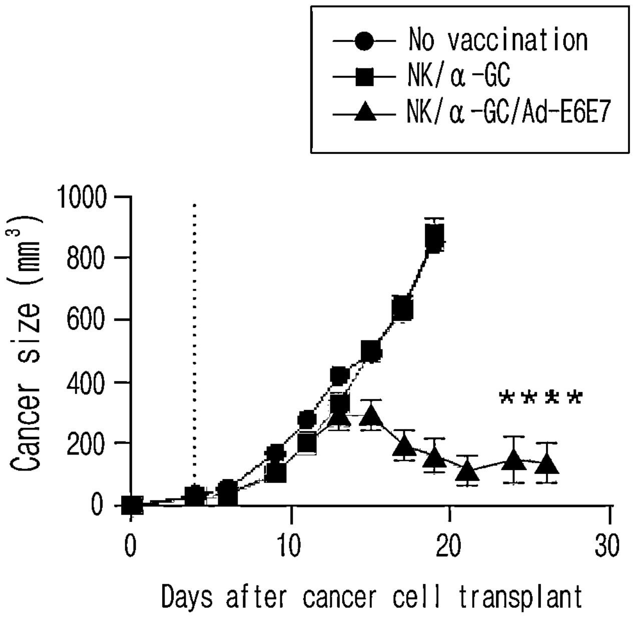
FIG. 3B is a graph showing the anticancer effect (change in tumor size) of the vaccine comprising natural killer cells loaded with α-GC and transected with adenovirus expressing antigens (NK/α-GC/Ad-E6E7).
Figure 3C:
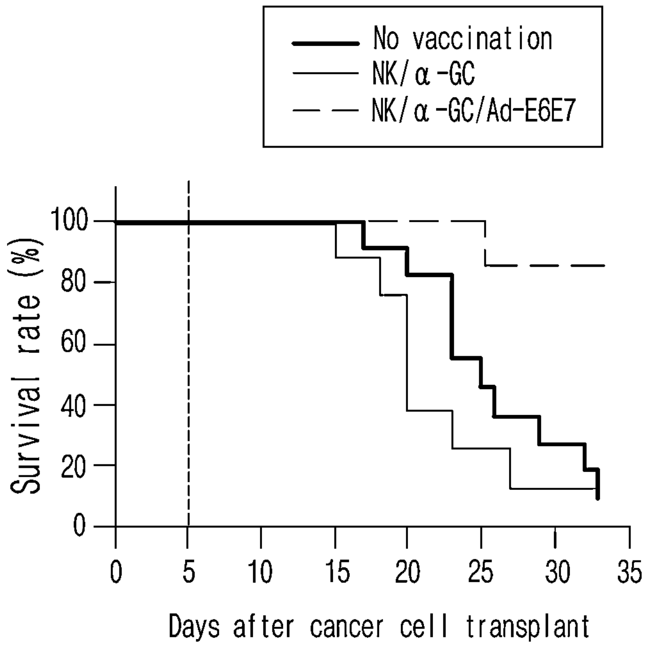
FIG. 3C is a graph showing the anticancer effect (mouse survival rate) of the vaccine comprising natural killer cells loaded with α-GC and transected with adenovirus expressing antigens (NK/α-GC/Ad-E6E7).

As a result, as shown in FIGS. 3B and 3C, when the natural killer cell vaccine (NK/α-GC/Ad-E6E7) was administered, cancer growth was suppressed and a high survival rate was observed. In contrast, in the mice administered with NK/α-GC, tumor growth was hardly inhibited and a low survival rate was observed.

Through the above results, it was confirmed that the anticancer therapeutic effect could not be induced by activating natural killer T cells and natural killer cells loaded with α-GC alone.

Experimental Example 2: Confirmation of Effectiveness of Natural Killer Cell Vaccine Loaded with Antigen Peptides <2-1> Confirmation of Induction of Cytotoxic T Cell Response The present inventors investigated whether the natural killer cell vaccine loaded with the antigen peptides of Example <1-2> could induce cytotoxic T cell responses.

Figure 4A:
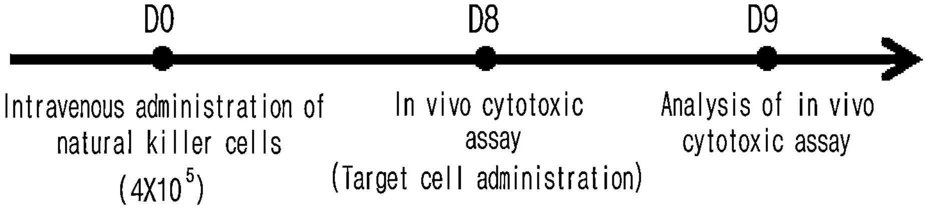
FIG. 4A is a diagram showing the experimental method for confirming the activation of antigen-specific cytotoxic T cells by the vaccine comprising natural killer cells co-loaded with α-GC and peptides.

C57BL/6 mice were immunized by intravenous administration of natural killer cells loaded with α-GC (NK/α-GC), natural killer cells loaded with OVA$_{257-264}$ peptide (NK/OVA pep), or natural killer cells loaded with α-GC and OVA$_{257-264}$ peptide together (NK/α-GC/OVA pep), and an in vivo cytotoxicity assay was performed 8 days later (FIG. 4A).

Figure 4B:
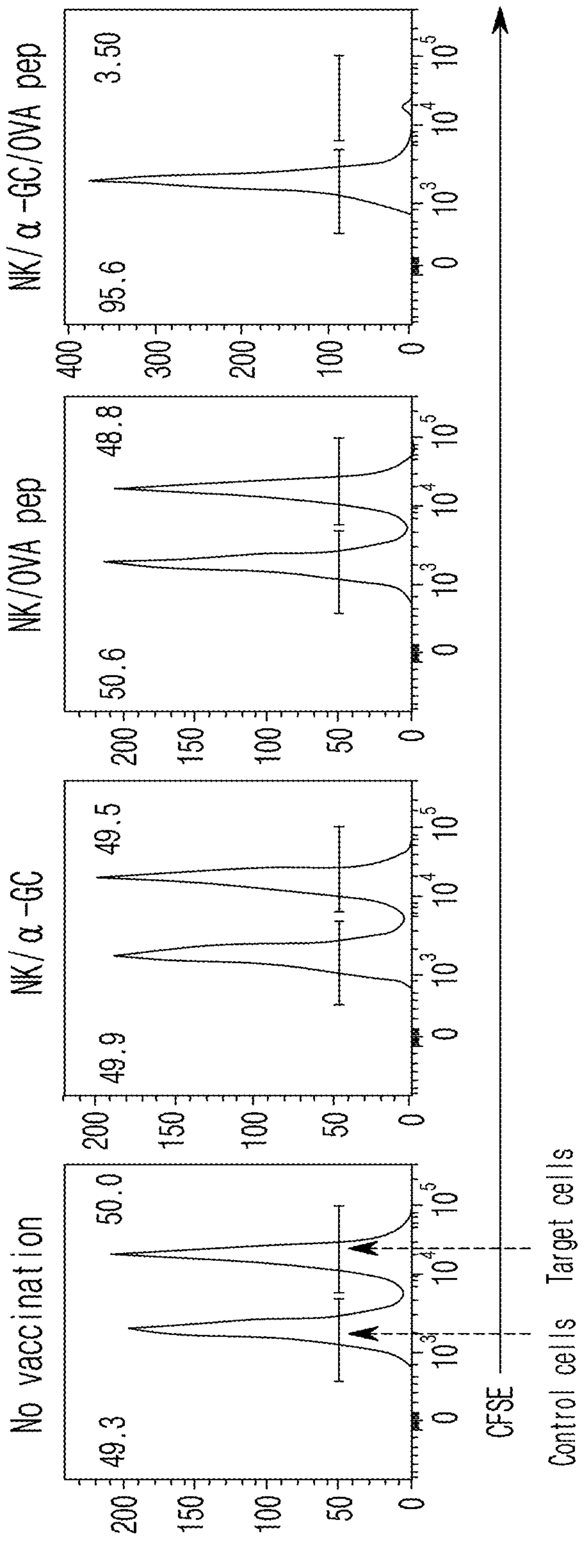
FIG. 4B is a set of histograms showing the in vivo cytotoxic T cell activity induced by the vaccine comprising natural killer cells loaded with α-GC (NK/α-GC), the vaccine comprising natural killer cells loaded with $ovalbumin_{257-264}$ peptide (NK/OVA pep), or the vaccine comprising natural killer cells co-loaded with α-GC and $ovalbumin_{257-264}$ peptide (NK/α-GC/OVA pep).
Figure 4C:
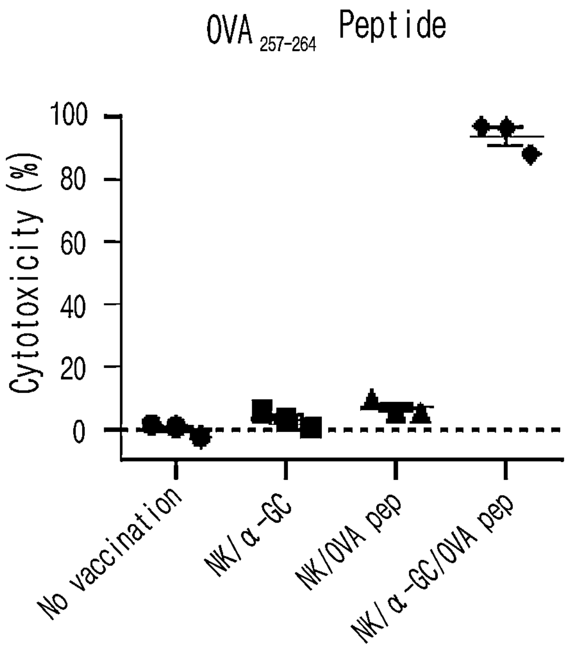
FIG. 4C is a graph showing the cytotoxic T cell activity of FIG. 4B.

As a result, as shown in FIGS. 4B and 4C, only in the mouse group administered with NK/α-GC/OVA pep, the CFSE$^{high}$ target cells loaded with OVA$_{257-264}$ peptide were mostly lysed. This confirmed that cytotoxic T cells can also be activated by the natural killer cell vaccine loaded with α-GC and peptides.

However, unlike that cytotoxic T cell responses were induced in the group administered with natural killer cells to which only the antigen was delivered via an adenovirus vector without α-GC in Experimental Example <1-2> (FIG. 2C), no cytotoxic T cell responses were observed in the group administered with NK/OVA pep loaded with peptide alone (FIG. 4C). This suggests that delivering the entire antigen via adenovirus to induce diverse immune responses specific to multiple epitopes is superior to presenting only a single peptide in inducing cytotoxic T cell immune responses.

<2-2> Evaluation of Anticancer Effect of Natural Killer Cell Vaccine

Figure 5A:
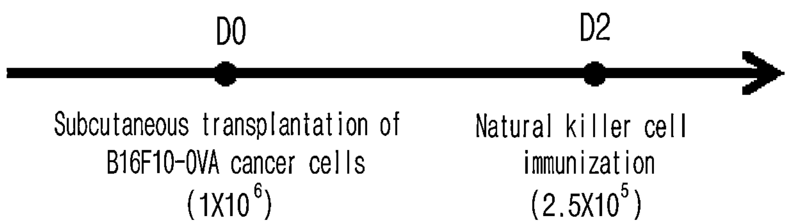
FIG. 5A is a diagram showing the experimental method for confirming the anticancer effect of the vaccine comprising natural killer cells co-loaded with α-GC and peptides.

The present inventors investigated whether the natural killer cell vaccine loaded with antigen peptides could induce anticancer therapeutic effects (FIG. 5A).

To this end, C57BL/6 mice were immunized with 2.5×10$^5$ NK/OVA pep or NK/α-GC/OVA pep 2 days after subcutaneous implantation of 1×10$^5$ B16F10-OVA cancer cells into the mice.

Figure 5B:
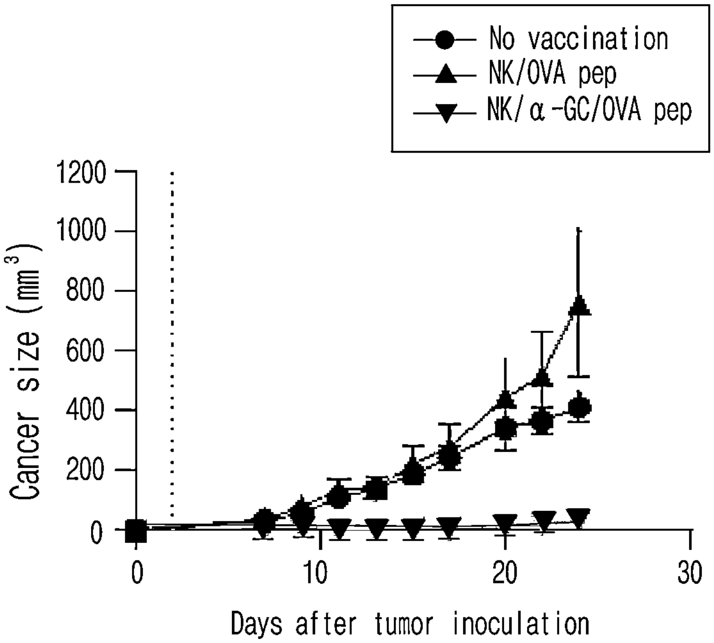
FIG. 5B is a graph showing the anticancer effect (change in tumor size) of the vaccine comprising natural killer cells co-loaded with α-GC and peptides (NK/α-GC/OVA pep).
Figure 5C:
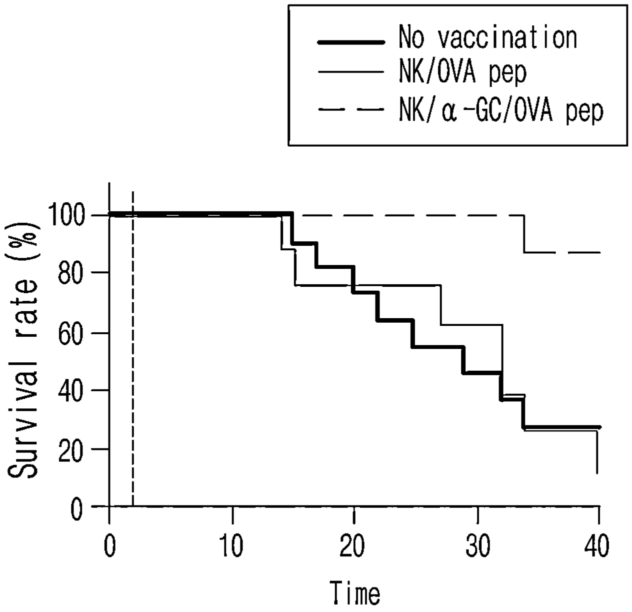
FIG. 5C is a graph showing the anticancer effect (mouse survival rate) of the vaccine comprising natural killer cells co-loaded with α-GC and peptides (NK/α-GC/OVA pep).

As a result, as shown in FIGS. 5B and 5C, when the natural killer cell vaccine (NK/α-GC/OVA pep) was administered, cancer growth was significantly suppressed and a high survival rate was observed. In contrast, in the mice administered with NK/OVA pep, tumor growth was hardly inhibited and a low survival rate was observed. Therefore, it was revealed that peptide loading alone cannot induce sufficient anticancer therapeutic effects.

When combined with the above results and the anticancer effect data of Examples <1-3> (FIGS. 3B and 3C), it was confirmed that the natural killer cell vaccine prepared by loading α-GC and delivering antigen showed a stronger anticancer effect than the cell vaccine loaded with α-GC alone or delivered with antigen alone, inhibiting cancer growth and improving survival rate.

What is claimed is:

1. An immunotherapeutic vaccine comprising natural killer cells loaded with natural killer T cell ligands and cancer antigens, wherein the natural killer T cell ligands are alpha-galactosylceramide, and wherein the cancer antigens are selected from the group consisting of gp 100 (glycoprotein 100, melanoma antigen gene (MAGE), human papilloma virus (HPV) E6/E7, tyrosinase, tyrosinase-related protein-1 (TRP-1), tyrosinase-related protein-2 (TRP-2), murinoglobulin 1 (MUC-1), carcinoembryonic antigen (CEA), p53, α-fetoprotein, Her-2/neu, proteinase 3, Wilms' Tumor 1 (WT-1), Prostatic Acid Phosphatase (PAP), Prostate-Specific Antigen (PSA), Prostate-Specific Membrane Antigen (PSMA), Carbonic Anhydrase IX (G250), B Melanoma Antigen (BAGE), Cancer/testis G Antigen (GAGE), New York Esophageal Squamous Cell Carcinoma 1 (NY-ESO-1), Melanoma Antigen Recognized by T cells 1 (MART-1), Melanocortin 1 Receptor (MC1R), Ig (Immunoglobulin) Idiotype, CDK4 (cyclin-dependent kinase 4), caspase-8, Beta-Catenin (β-catenin), Cancer Immuno-Antigen (CIA), Breakpoint Cluster Region-Abelson (BCR/ABL), Epstein-Barr Virus Latent Membrane Protein 2A (EBV LMP2a), Hepatitis C Virus (HCV), Human Herpesvirus 8 (HHV-8), 5T4 Oncofetal Antigen (5T4), and tumor-specific mutation-derived neoantigens.

2. The immunotherapeutic and preventive vaccine according to claim 1, wherein the cancer antigens are in a form of a peptide, a lipopolysaccharide, a polysaccharide, a glycoprotein, or a polynucleotide.

3. The immunotherapeutic vaccine according to claim 2, wherein the polynucleotide is DNA or RNA.

4. The immunotherapeutic vaccine according to claim 1, wherein the cancer antigens are introduced into the natural killer cells by a recombinant virus and expressed.

5. The immunotherapeutic vaccine according to claim 4, wherein the recombinant virus is adenovirus, retrovirus, vaccinia virus, pox virus, or Sindbis virus into which a gene expressing the cancer antigens has been introduced.

* * * * *